United States Patent
Laursen et al.

(10) Patent No.: US 6,762,602 B1
(45) Date of Patent: Jul. 13, 2004

(54) DEVICE FOR INSPECTING CONDUITS MADE FROM FERROMAGNETIC MATERIALS

(75) Inventors: Poul Laursen, Don Mills (CA); Christopher Meredith, Georgetown (CA)

(73) Assignee: PII Pipetronix GmbH, Stutensee (DE)

( * ) Notice: Subject to any disclaimer, the term of this patent is extended or adjusted under 35 U.S.C. 154(b) by 423 days.

(21) Appl. No.: 09/598,684

(22) Filed: Jun. 21, 2000

(30) Foreign Application Priority Data

Jun. 25, 1999 (DE) .......................................... 199 29 072

(51) Int. Cl.[7] .......................... G01N 27/82; F16L 55/44
(52) U.S. Cl. ..................................... 324/220; 73/866.5
(58) Field of Search ................................ 324/220, 221; 73/865.8, 866.5, 86

(56) References Cited

U.S. PATENT DOCUMENTS

| | | | | |
|---|---|---|---|---|
| 2,698,920 A | * | 1/1955 | Gieske ......................... | 324/221 |
| 4,447,777 A | * | 5/1984 | Sharp et al. ................. | 324/220 |
| 4,506,219 A | * | 3/1985 | Lee .............................. | 324/221 |
| 4,649,343 A | | 3/1987 | Birchak ....................... | 324/220 |
| 5,115,196 A | * | 5/1992 | Low et al. ................... | 324/262 X |
| 5,426,367 A | * | 6/1995 | Martin et al. ............... | 324/221 X |
| 5,454,276 A | * | 10/1995 | Wernicke ................... | 324/226 X |
| 5,537,035 A | | 7/1996 | Fowler ....................... | 324/220 |
| 5,747,998 A | * | 5/1998 | Fowler et al. .............. | 324/220 X |
| 6,009,756 A | * | 1/2000 | Willems et al. ............ | 73/628 X |
| 6,100,684 A | * | 8/2000 | Ramaut ....................... | 324/220 |
| 2001/0017541 A1 | * | 8/2001 | Kwun et al. ............... | 324/220 X |

FOREIGN PATENT DOCUMENTS

EP   0 775 910   5/1997 .......... G01N/29/27

* cited by examiner

Primary Examiner—Thomas P. Noland

(57) ABSTRACT

The invention proposes a device, e.g. an inspection pig, for inspecting conduits made from ferromagnetic materials, such as pipelines, for faults, cracks, corrosion or the like, comprising at least one pulling element, a supporting structure of variable circumference, disposed on the pulling element and comprising substantially radially disposed supporting arms each of which is pivotable about axes disposed perpendicular to the longitudinal central axis of the pulling element, and several permanent magnets disposed at the circumference of the supporting structure for generating a magnetic field, and with sensors. For strengthening or weakening the magnetic field generated by the permanent magnets in dependence on the circumference of the supporting structure or in dependence on the lateral separation between the permanent magnets, the permanent magnets are associated with further magnets having a magnetic field which can be varied in direction or strength. In an embodiment, the further magnets associated with the permanent magnets are permanent magnets, wherein the direction of their magnetic field can be changed by turning using an electric or mechanical actuator. In another embodiment coils are used as magnets, which can be supplied with a variable current.

21 Claims, 3 Drawing Sheets

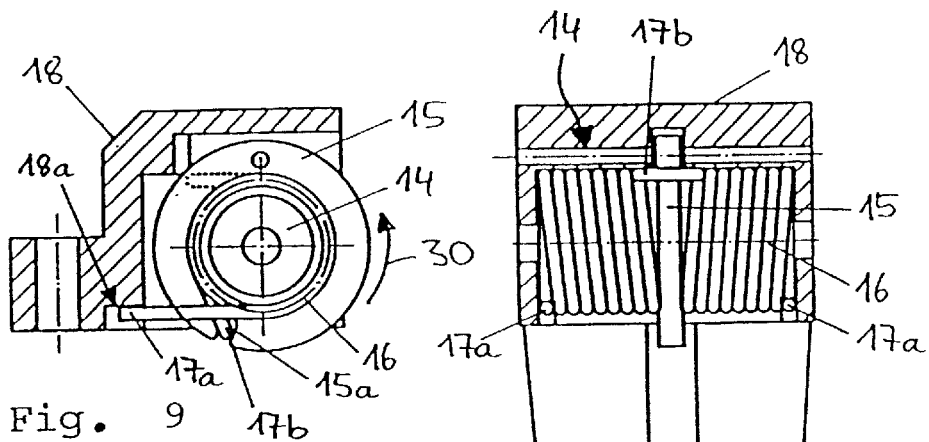
Fig. 9
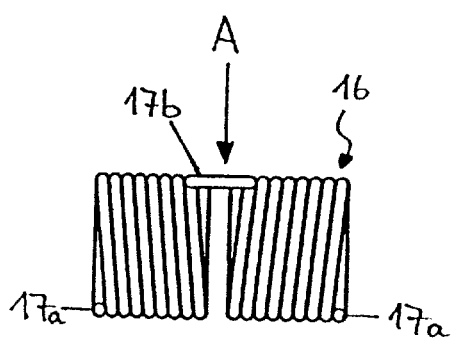
Fig. 10
Fig. 11
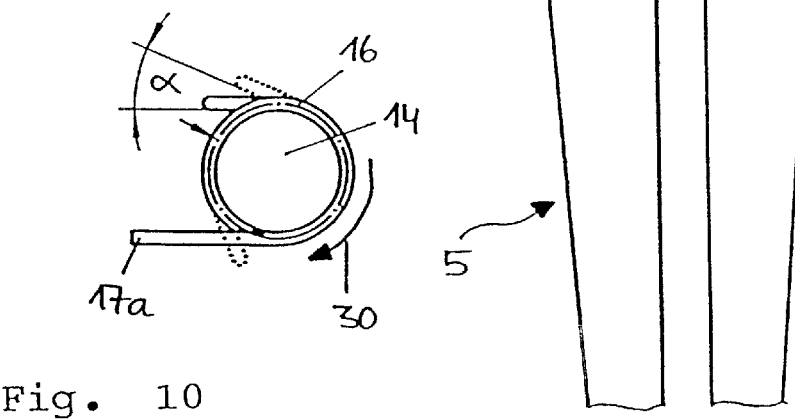
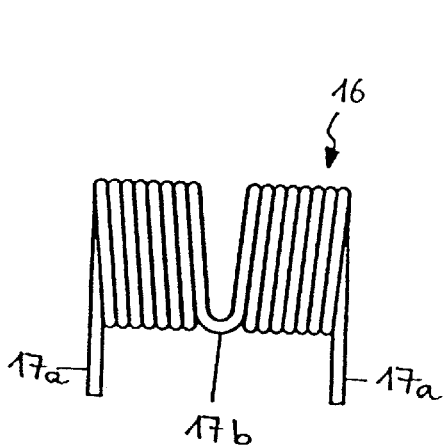
Fig. 12
Fig. 13

DEVICE FOR INSPECTING CONDUITS MADE FROM FERROMAGNETIC MATERIALS

This application claims Paris Convention priority of DE 199 29 072.5 filed Jun. 25, 1999 the complete disclosure of which is hereby incorporated by reference.

BACKGROUND OF THE INVENTION

The invention concerns a device, e.g. an inspection pig, for inspecting conduits made from ferromagnetic materials, such as pipelines, for faults, cracks, corrosion or the like, comprising at least one pulling element, a supporting structure with variable circumference, disposed on the pulling element, and comprising substantially radially disposed supporting arms pivotable about axes disposed perpendicular to the longitudinal central axis of the pulling element, and several permanent magnets disposed on the circumference of the supporting structure for generating a magnetic field, and also having sensors.

So-called inspection pigs are used for inspecting conduits, in particular for transporting water, oil or gas, comprising inspecting means with inspecting elements or sensors, disposed at the outer circumference for inspecting the state of the conduit walls. The sensors can be of various designs. Conventional sensors are i.a. piezo-electrical, electro-acoustic, and electromagnetic sensors such as Hall, stray flux and eddy current sensors.

Different wall conditions or wall thickness reductions, e.g. due to corrosion etc. provide different signals which can be further processed e.g. in an electronic unit.

Conventional inspection pigs for inspecting conduits of different standard widths, or for introducing the inspection pigs via supply lines into the conduit to be inspected, comprise radially expandable supporting structures disposed on a central pulling element with inspecting elements and/or sensors at their circumference. Such supporting structures have a circumference which can vary in dependence on the inner cross-section of the conduit and comprise e.g. several substantially radially disposed supporting arms pivotable about axes disposed perpendicular to the longitudinal central axis of the pulling element (DE 197 46 510 A1, DE 197 46 511 A1).

EP 0 775 910 A1 describes a device for inspecting ferromagnetic materials, in particular conduits, with a radio frequency current coil which serves, in connection with a magnetic field, for excitation or detection of ultra sound waves, wherein the magnetic field is substantially generated by permanent magnets disposed at the circumference of the conduit. An additional magnet arrangement generates a background magnetic field.

These above mentioned devices, based on an electromagnetic measuring principle, have the disadvantage that the magnetic field of the permanent magnets disposed at the circumference of the supporting structure depends on their lateral separation and on the cross-section of the respective conduit, wherein the density of the magnetic field is higher or the magnetic field strength is higher, the smaller the lateral separation between the permanent magnets or the smaller the cross-section of the respective conduit. Consequently, the measuring sensitivity decreases with increasing cross-section of the respective conduit. Moreover, conduits with varying cross-section do not have comparable measuring results and are subject to differing measurement errors.

It is the underlying purpose of the present invention to avoid these disadvantages in a simple and inexpensive fashion.

SUMMARY OF THE INVENTION

This object is achieved in accordance with the invention by a device of the above mentioned kind in that at least some of the permanent magnets are associated with a further magnet having a variable magnetic field for strengthening and/or weakening the magnetic field generated by the permanent magnet in dependence on the circumference of the supporting structure or in dependence on the lateral separation between the permanent magnets.

In a device in accordance with the invention, the magnetic field generated by the permanent magnets can be strengthened or weakened by changing the direction and/or the strength of the magnetic field of the magnets associated with the permanent magnets. In this fashion a magnetic field with a substantially constant magnetic field strength can be obtained for conduits of any cross-section irrespective of the lateral separation between the permanent magnets. For reasons of symmetry, one magnet with a variable magnetic field is associated with each permanent magnet.

A first variant of the embodiment provides that the magnet with variable magnetic field is also a permanent magnet which can be turned by means of an actuator for changing the direction of its magnetic field. Turning of the poles of the magnets can thereby move same e.g. into a position aligned with the orientation of the poles of the permanent magnets to optimally increase the magnetic field generated by the permanent magnets for inspecting conduits with large standard width. Conversely, the magnetic field generated by the permanent magnets can e.g. be weakened to a maximum extent if the rotatable magnets and their poles are moved to an orientation opposite to the poles of the permanent magnets to weaken the magnetic field generated by the permanent magnet for inspecting a conduit with small standard width. By turning the magnets, their magnetic field lines can be oriented at an arbitrary angle with respect to the field lines of the magnetic fields generated by the permanent magnets to thereby strengthen or weaken same in a variable fashion.

The actuator can comprise at least one toothed wheel engaging the rotatable magnet, which can e.g. be formed as a shaft which is rotatably disposed and connected to such a toothed wheel for secure mutual rotation. In this case, the rotatable magnet also comprises a toothed wheel connected for secure rotation therewith. Alternatively, the rotatable magnet, e.g. of cylindrical shape, has a toothing at its circumference.

In a preferred embodiment, the actuator can be driven electrically. The actuator can be driven e.g. by an electric motor which communicates with at least one sensor element for detecting the circumference of the supporting structure or the lateral separation between the permanent magnets.

In accordance with a further preferred embodiment, the actuator is mechanically driven. Such a purely mechanical drive has, in particular, the advantage that no additional, in particular, electrical driving means are required. It is therefore very inexpensive and no additional drive or current supply means are required for the arrangement.

In a preferred embodiment, the mechanically driven actuator is driven by at least one helical spring which resiliently biases the supporting arms laterally outwardly at the circumference of the supporting structure and, with lateral approach or withdrawal of the supporting arms, converts the length change associated with its compression or expansion, into a rotary motion of the actuator.

A second variant of the embodiment provides that the magnet of variable magnetic field is an electromagnet, e.g. an induction coil, which can be supplied with a variable current to change the magnetic field strength. In this case, the induction coil magnets can be supplied e.g. with an induction current inducing a magnetic field oriented in the direction of the magnetic field of the permanent magnets to increase same for inspecting a conduit with large standard width. Conversely, the magnetic field generated by the permanent magnets can be weakened by supplying an opposite induction current to the induction coil to weaken the magnetic field generated by the permanent magnets for inspecting a conduit with small standard width. The induction coils preferably communicate with at least one sensor element for determining the circumference of the supporting structure or the lateral separation between the permanent magnets for varying the strength and/or direction of the induction current depending on the cross-section of the conduit.

Each permanent magnet at the circumference of the supporting structure preferably has an associated longitudinally disposed further permanent magnet for generating a magnetic field extending substantially parallel to the longitudinal central axis of the pulling element. This generates a substantially homogeneous magnetic field with substantially parallel field lines about the entire circumference of the pipe section to be inspected. Advantageously, both permanent magnets are each associated with a further magnet having a magnetic field which can be varied in direction and/or strength.

The magnetising units, each formed by a permanent magnet and a magnet associated therewith having a variable magnetic field are preferentially disposed on parallelogram supports each of which pivots on two supporting arms disposed one after the other. This ensures that the magnetic field lines always extend in the same direction with respect to the conduit walls to be inspected, e.g. essentially parallel to the longitudinal central axis of the conduit.

The parallelogram supports are preferably resiliently biased laterally in an outward direction via spring jaws such that the supporting structure automatically adjusts to conduits with various cross-sections.

In a preferred embodiment, the spring jaws accommodate several laterally separated sensors for inspecting the condition of the conduit walls. The sensors are preferably disposed between the spring jaws via spring elements, wherein the respective mutual lateral separations between the sensors are equal for any circumference of the supporting structure. This ensures highest possible measuring accuracy and measuring sensitivity of the device in accordance with the invention in that the magnetising units provide a magnetic field whose strength is substantially independent of the diameter of the conduit and the sensors are each disposed at constant lateral separations to detect the smallest of signals produced by differing wall conditions in the conduit.

Alternatively or additionally, each supporting arm can be radially outwardly biased by a spring force, e.g. by means of a disc spring set.

Each supporting arm and/or each parallelogram support preferably comprises at least one supporting roller for guidance on the inner conduit wall disposed, for the case of the supporting arm, at its outer end in the region of the pivot axis of the parallelogram support.

In a further development of the inventive device, the supporting arms and/or the parallelogram supports are synchronized. In this fashion, the device is also suitable for use in conduits or pipelines comprising branches e.g. Y- or T-shaped branches. During passage of an inspection pig through such branches, those radially outwardly biased supporting arms or parallelogram supports which do not experience a counter pressure from the pipe inner wall due to the branching are held by neighboring supporting arms or parallelogram supports which abut on the pipe wall opposite to the branch, such that the free supporting arms or parallelogram supports cannot spring out radially. In this manner, damage to the inspecting elements, in particular to those disposed on the parallelogram supports, is prevented.

Moreover, the magnetic field required for inspection during passage of the inspection pig through pipe branches, is thereby not impaired. Each pair of neighboring supporting arms and/or each pair of neighboring parallelogram supports are preferably synchronized to ensure an angular difference between the supporting arms relative to the longitudinal central axis of the pulling element of between 1° and 5°, in particular between 2° and 3°.

In a preferred embodiment, the supporting arms of the supporting structure are mounted to the pulling element via a central sleeve which can be fixed to the pulling element. The central sleeve can thereby be fixed to the pulling element in a radially pivotable fashion, e.g. via a ball and socket joint to facilitate passage of the inspection pig through pipe bends.

The invention is described in more detail below by means of preferred embodiments with reference to the drawing.

BRIEF DESCRIPTION OF THE DRAWING

FIG. 9 shows a side view of an actuator in accordance with FIG. 8;

FIG. 10 shows a schematic view of an actuator in accordance with FIGS. 8 and 9;

FIG. 11 shows a top view of an actuator in accordance with FIGS. 8 through 10;

FIG. 12 shows a side view of a helical spring for an actuator in accordance with FIGS. 8 through 11; and FIG. 13 shows a side view of a helical spring in accordance with FIG. 12 in the direction of arrow A.

DESCRIPTION OF THE PREFERRED EMBODIMENT

Figure 1:
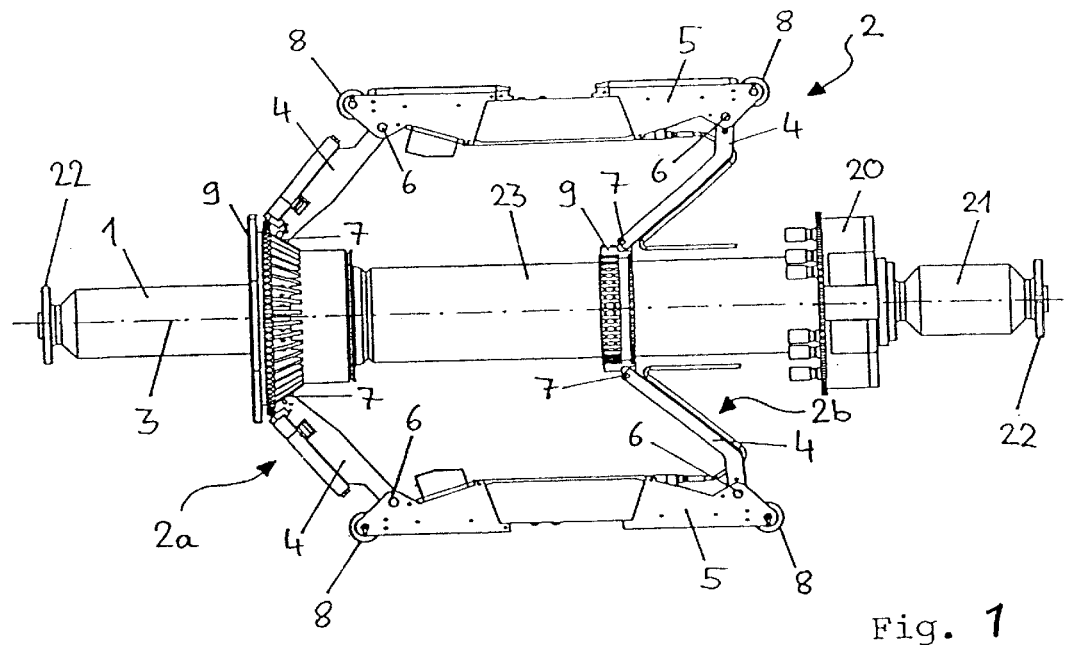
FIG. 1 shows a side view of an embodiment of an inventive device with a supporting structure comprising a parallelogram support.

The device shown in FIG. 1 for inspecting conduits, such as pipelines, for faults, cracks, corrosion or the like, comprises a pulling element 1 and a supporting structure 2 disposed thereon. The supporting structure 2 comprises two collars 2a, 2b disposed one after another, with supporting arms 4, each disposed substantially radially and being pivotable about the axes 7, disposed perpendicular to the longitudinal central axis 3 of the pulling element 1. The supporting arms 4 of each collar 2a, 2b are each fixed to the pulling element 1 via a central sleeve 9 disposed on a central body 23. Each collar 2a, 2b can comprise e.g. twelve supporting arms 4. Each supporting arm 4 of the collar 2a is connected to one supporting arm 4 of the collar 2b via a parallelogram support 5, pivoted parallel to the longitudinal central axis 3 of the pulling element 1, about pivot axes 6, disposed at the ends of the supporting arms 4. The supporting arms 4 are biased radially outwardly e.g. by one disc spring set (not shown) each, such that supporting rollers 8 disposed on the parallelogram supports 5 always seat on the inner side of conduits (not shown) having differing cross-sections. The central sleeves 9 can be connected either rigidly to the pulling element 1 or one or both central sleeves 9 are mounted on the pulling element 1 for radial pivoting, e.g. by means of a ball bearing, to facilitate passage of the device through pipe bends. The supporting arms 4 and/or the parallelogram supports 5 are synchronized to prevent springing out of individual supporting arms 4 or individual parallelogram supports 5 pivoted on the supporting arms 4, e.g. during passage of the device through Y- or T-shaped pipe branches. Towards this end, in particular two neighboring supporting arms 4 and/or parallelogram supports 5 are each synchronized thereby ensuring an angular deviation between the supporting arms 4 and the longitudinal central axis 3 of the pulling element 1 of between 1° and 5°.

For connecting the device e.g. to a pig for moving same through a conduit, the two ends of the pulling element 1 are provided with coupling pieces 22 of which e.g. the right coupling piece is connected via a pivotable coupling device 21 and a connecting means 20 to the pulling element 1.

Figure 2:
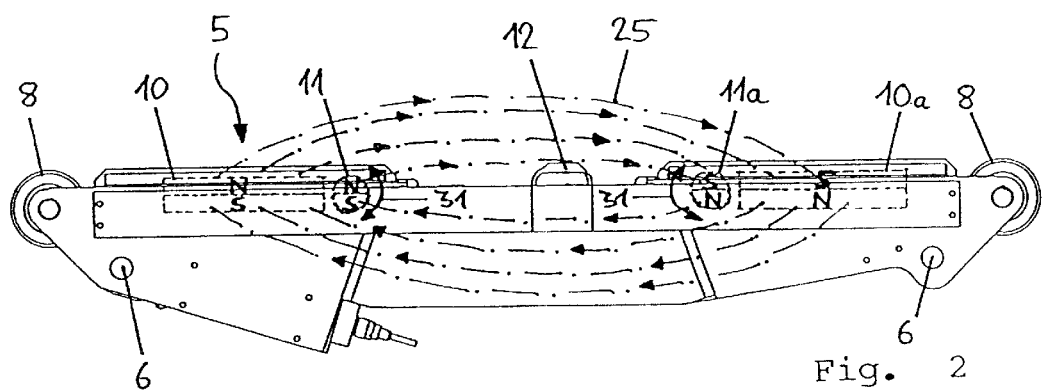
FIG. 2 shows a side view of an embodiment of a parallelogram support.

FIG. 2 shows two permanent magnets 10, 10a disposed on each parallelogram support 5 which generate a magnetic field (indicated with the field lines 25). Cracks or corrosion of the conduit influence the magnetic field and such faults are detected by electromagnetic sensors 12, such as Hall, stray flux, eddy current sensors or the like, disposed on the parallelogram supports 5 with optional further processing of the various signals in an electronic unit (not shown). The magnetic field lines 25 extend substantially parallel to the longitudinal central axis of the pulling element. To strengthen and/or weaken the magnetic field generated by the permanent magnets 10, 10a in dependence on the circumference of the supporting structure 2 or in dependence on the inner cross-section of the conduit, and to thereby provide a magnetic field of substantially constant strength which is substantially independent of the lateral separation between the permanent magnets 10, 10a disposed on two neighboring parallelogram supports 5, each permanent magnet 10, 10a is associated with a further magnet 11, 11a which, in the embodiment shown, is also a permanent magnet the magnetic field of which can be changed by changing its direction, namely by turning the magnet 11, 11a in the direction of arrow 31. The orientation of the magnet poles (N, S) of the magnets 11, 11a in the position shown in FIG. 2 corresponds to the orientation of the magnet poles (N, S) of the permanent magnets 10, 10a thereby increasing their magnetic field to a maximum which is required e.g. in conduits of large cross-section or with large separation between the permanent magnets 10, 10a.

Figure 3:
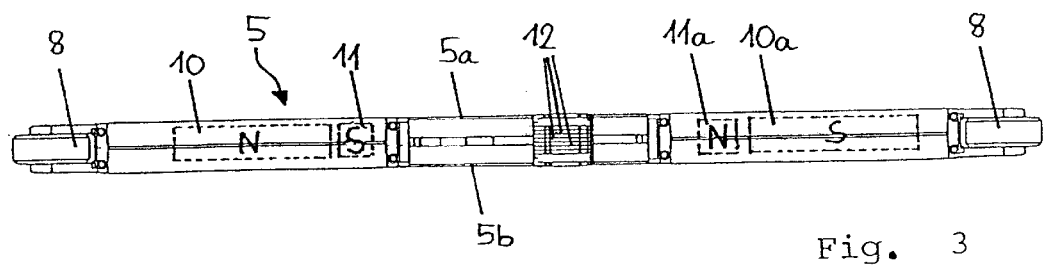
FIG. 3 shows a top view onto a parallelogram support in accordance with FIG. 2 with small circumference of the supporting structure.
Figure 4:
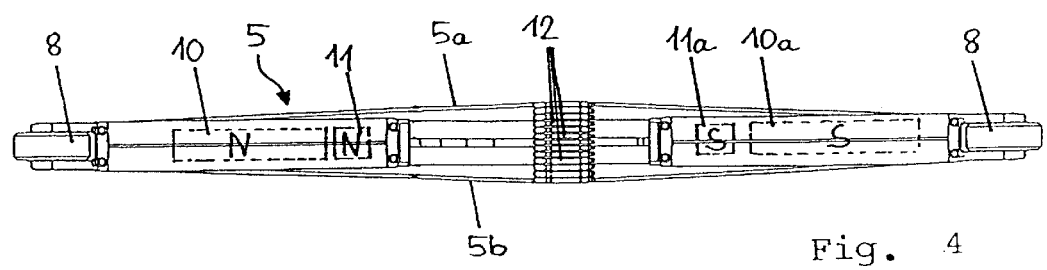
FIG. 4 shows a top view of a parallelogram support in accordance with FIG. 2 with large circumference of the supporting structure.

FIGS. 3 and 4 each show a top view of such a parallelogram support 5 which, in the embodiment shown, is laterally, outwardly biased by laterally disposed spring jaws 5a, 5b such that the flexible spring jaws 5a, 5b abut in conduits of small cross-section (FIG. 3), e.g. of a cross-section of 28 inches, as well as in conduits of large cross-section (FIG. 4), e.g. of 42 inches. Several sensors 12, laterally separated by spring elements (not shown), are disposed between the spring jaws 5a, 5b, wherein the respective mutual lateral separation between sensors 12 is constant both for a small circumference of the supporting structure (FIG. 3) as well as for large circumference of the supporting structure (FIG. 4).

In FIG. 3, the magnet poles (N, S) of the rotatable magnets 11, 11a are oriented opposite to the magnet poles (N, S) of the permanent magnets 10, 10a, thereby weakening their magnetic field to a maximum degree. In the arrangement shown in FIG. 4, the magnet poles (N, S) of the rotatable magnets 11, 11a are oriented in correspondence with the magnet poles (N, S) of the permanent magnets 10, 10a thereby increasing their magnetic field to a maximum degree.

Figure 5:
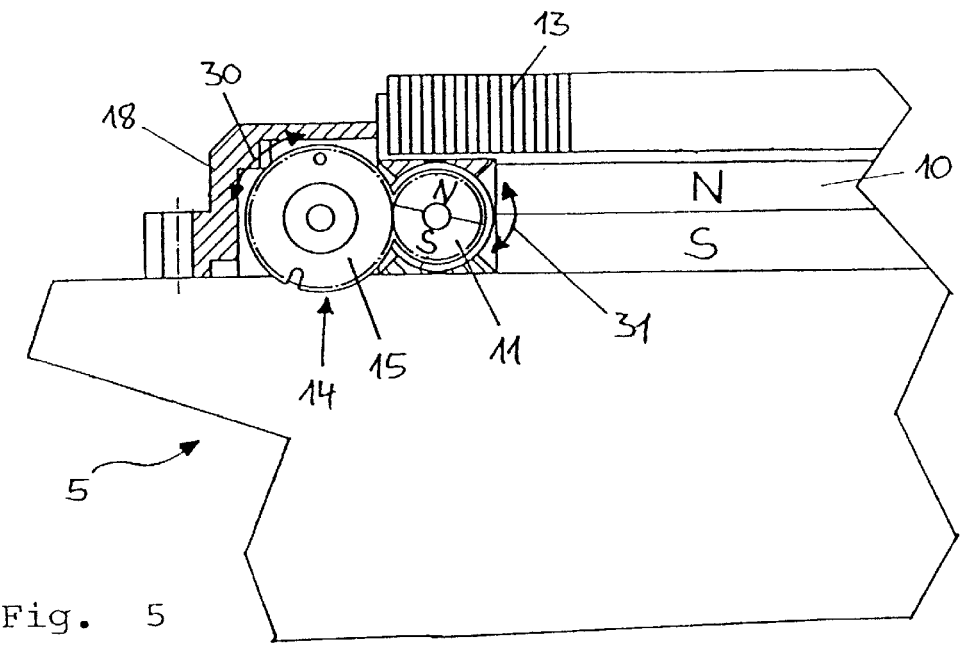
FIG. 5 shows a side view of a detailed section through a parallelogram support in accordance with FIG. 2.

FIG. 5 shows a detailed section through a parallelogram support 5. The magnet 11 associated with the permanent magnet 10 is rotatable in the direction of the arrow 31 by means of an actuator 14, wherein the actuator 14 comprises a toothed wheel 15 engaging in the magnet 11. The actuator 14 is designed e.g. as a shaft disposed in a recepticle 18 and connected to the toothed wheel 15 for secure mutual rotation. A brush provides protection from soiling, humidity or the like and is disposed above the rotatable magnet 11 and the permanent magnet 10.

Figure 6:
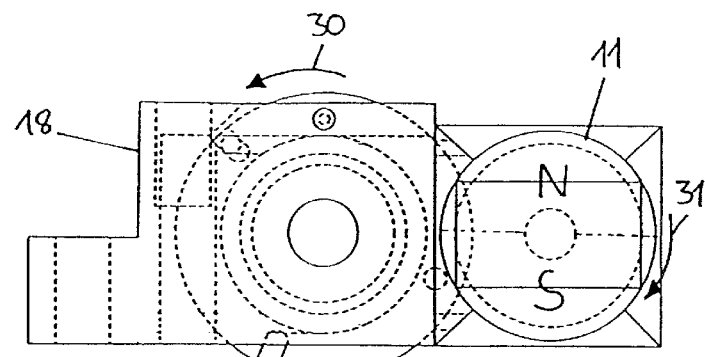
FIG. 6 shows a side view of an electrically driven actuator for changing the direction of the magnetic field of a magnet with variable magnetic field.
Figure 7:
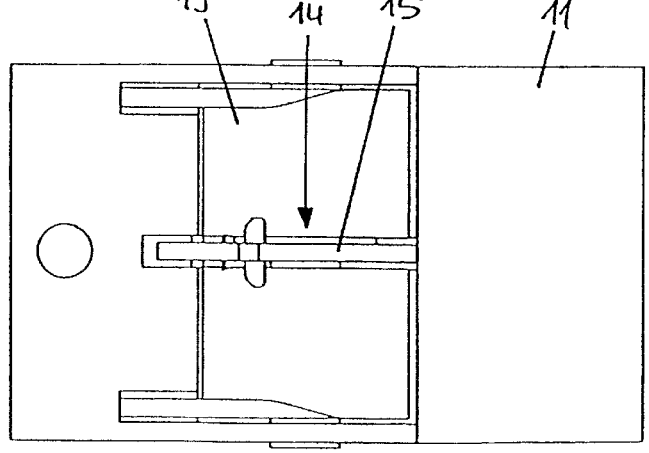
FIG. 7 shows a top view of an actuator in accordance with FIG. 6.

The embodiment of an electrically driven actuator 14 shown from the side in FIG. 6 and from the top in FIG. 7, comprises an electric motor 19 for driving the toothed wheel 15 engaging the magnet 11. The electric motor 19 is connected to an appropriate electric, electronic or mechanical sensor element for determining the circumference of the supporting structure 2 (FIG. 1) or for determining the lateral separation between the parallelogram supports 5 (FIG. 2). A mechanical sensor element can be realized e.g. in the form of the spring jaws 5a, 5b (FIGS. 3 and 4).

Figure 8:
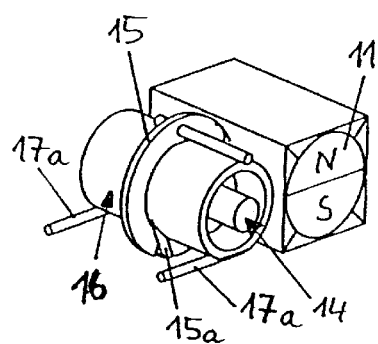
FIG. 8 shows a perspective view of a mechanically driven actuator for changing the direction of the magnetic field of a magnet with variable magnetic field.

The actuator 14 in accordance with FIG. 8 also comprises a toothed wheel 15 engaging the magnet 11, and is driven purely mechanically by a helical spring 16 which elastically and laterally outwardly biases the supporting arms or parallelogram supports (not shown) to convert the length change which occurs during lateral approach of the supporting arms or the parallelogram supports or during lateral separation thereof, in association with its compression or expansion, into a rotary motion of the actuator 14 or of the toothed wheel 15 connected therewith for secure mutual rotation. Towards this end, the helical spring 16 is disposed coaxially with the actuator 15 and engages with two supporting ends 17a into a recess 18a formed at the inside of the recepticle 18 (FIG. 9), wherein a central working section 17b of the helical spring 16 engages in a radial groove 15a formed in the actuator 14 or in the toothed wheel 15.

When the helical spring 16 is e.g. compressed, its supporting ends are supported in the recess 18a of the recepticle 18 and the working section 17b begins to turn the toothed wheel 15 in the direction of arrow 30. When the helical spring 16 expands, it turns the toothed wheel 15 in the opposite direction. In this fashion, the angle of rotation α (FIG. 10) of the actuator 14 is proportional to the length change of the helical spring 16. The angle of rotation α of the actuator 14 can transmit a larger, a smaller or the same angle of rotation α to the magnet 11 by varying the toothing of the toothed wheel 15 or by varying its diameter.

FIG. 11 shows a top view of the helical spring 16, which is disposed coaxially with respect to the actuator 14, wherein its working section 17b is connected to the toothed wheel 15 and its supporting ends 17a are supported in the recepticle 18 (shown in a sectional view). This embodiment having purely mechanical drive of the actuator 14, can comprise helical springs 16 in addition to the spring jaws 5a, 5b (FIGS. 3 and 4) which laterally, outwardly bias the parallelogram supports 5.

FIGS. 12 and 13 are side views of the helical spring 16 prior to assembly.

List of Reference Numerals

1 pulling element
2 supporting structure
2a, 2b collar
3 longitudinal central axis of the pulling element
4 supporting arm
5 parallelogram support
5a, 5b spring jaws
6 pivot axis of the parallelogram support
7 pivot axis of the supporting arm
8 supporting roller
9 central sleeve
10, 10a permanent magnet
11, 11a magnet with variable magnetic field
12 sensor
13 brush
14 actuator
15 toothed wheel
15a groove
16 helical spring
17a supporting end of the helical spring
17b working section of the helical spring
18 recepticle
19 electric motor
20 connecting means
21 coupling means
22 coupling piece
23 central body
25 magnetic field lines

We claim:

1. An inspection device for conduits made from ferromagnetic materials and for pipelines, the device for inspection of faults, cracks and corrosion, the device comprising:

a pulling element having a longitudinal central axis;

pivot axes disposed on said pulling element, said pivot axes extending transverse to said longitudinal central axis;

a supporting structure of variable circumference, said supporting structure mounted to said pivot axes for pivoting, said supporting structure having substantially radially disposed supporting arms cooperating with said pivot axes;

a plurality of first permanent magnets mounted at an outer region of said supporting structure, the first permanent magnets for generating a first magnetic field;

sensors disposed at said outer region of said supporting structure; and a plurality of second magnets, wherein each one of said first permanent magnets has an associated second magnet with a variable second magnetic field and disposed proximate thereto for at least one of strengthening and weakening said first magnetic field in dependence on at least one of a circumference of said supporting structure and a lateral separation between the first magnets.

2. The device of claim 1, wherein said second magnets are second permanent magnets and further comprising actuators, said actuators communicating with said second permanent magnets for rotation thereof to change said second magnetic field.

3. The device of claim 2, wherein said actuators comprise at least one toothed wheel engaging said second permanent magnets.

4. The device of claim 2, wherein said actuators are electrically driven.

5. The device of claim 4, wherein said actuators are electrically driven by electric motors communicating with sensor elements for determining at least one of said circumference of said supporting structure and said lateral separation between said first permanent magnets.

6. The device of claim 2, wherein said actuators are driven by mechanical driving means.

7. The device of claim 6, wherein said mechanical driving means comprise at least one helical spring mounted at a circumference of said supporting structure to resiliently bias said supporting arms laterally and outwardly, wherein a lateral approach and a lateral separation of said supporting arms converts a length change occurring during compression and expansion of said helical spring into a rotational motion of said actuators.

8. The device of claim 1, wherein said second magnets are one of electric magnets and induction coils, said second magnets being driven with a variable current for changing a strength of said second magnetic field.

9. The device of claim 1, wherein each of said first magnets has an associated longitudinally displaced third permanent magnet for generating, together with said first magnets, a third magnetic field extending substantially parallel to said longitudinal central axis.

10. The device of claim 9, wherein each of the third magnets has an associated one of said second magnets having said variable second magnetic field.

11. The device of claim 1, wherein said supporting structure comprises parallelogram supports each of which is pivoted on two of said supporting arms, disposed one behind the other.

12. The device of claim 11, where said parallelogram supports are resiliently biased in a lateral, outward direction via spring jaws.

13. The device of claim 12, wherein said spring jaws accept several laterally separated sensors for inspecting a state of conduit walls.

14. The device of claim 13, wherein said sensors are disposed between said spring jaws via spring elements, wherein a mutual respective lateral separation between said sensors is constant for each supporting structure circumference.

15. The device of claim 11, further comprising at least one supporting roller disposed at one of an outer end of each supporting arm proximate a pivot axis of said parallelogram supports and at each parallelogram support, said at least one supporting roller for guidance on an inner wall of the conduit.

16. The device of claim 11, wherein at least one of said supporting arms and said parallelogram supports are synchronized.

17. The device of claim 16, wherein at least one of pairs of neighboring supporting arms and pairs of neighboring parallelogram supports are synchronized to ensure angles between said supporting arms and said longitudinal central axis of said pulling element which differ by between 1° to 5°.

18. The device of claim 17, wherein said angles differ by between 2° and 3°.

19. The device of claim 1, wherein said supporting arms are radially biased in an outward direction by a spring force.

20. The device of claim 19, wherein each of said supporting arms is biased by a disc spring set.

21. The device of claim 1, further comprising a central sleeve cooperating with said pulling element, wherein said supporting arms are mounted to said central sleeve.

* * * * *